(12) United States Patent
Yamaguchi

(10) Patent No.: US 6,732,001 B2
(45) Date of Patent: May 4, 2004

(54) PRODUCTION MANAGEMENT METHOD

(75) Inventor: Shingo Yamaguchi, Kyoto (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 10/379,091

(22) Filed: Mar. 3, 2003

(65) Prior Publication Data

US 2003/0187536 A1 Oct. 2, 2003

(30) Foreign Application Priority Data

Mar. 28, 2002 (JP) ........................................ 2002-092572

(51) Int. Cl.[7] .............................................. G06F 19/00
(52) U.S. Cl. ...................... 700/109; 700/100; 700/121; 73/865.8
(58) Field of Search ................................ 700/109, 121, 700/99, 100, 214; 73/865.8; 414/935

(56) References Cited

U.S. PATENT DOCUMENTS 6,018,688 A    1/2000  Hashimoto
6,073,501 A  * 6/2000  Rohner ...................... 73/865.8
6,449,522 B1 * 9/2002  Conboy et al. ............. 700/121

FOREIGN PATENT DOCUMENTS

JP          11084012 A  *  9/1997  ............. G01T/1/00

* cited by examiner

*Primary Examiner*—Albert W. Paladini
(74) *Attorney, Agent, or Firm*—Merchant & Gould P.C.

(57) ABSTRACT

With respect to production equipment for performing a plurality of production operations having different processing conditions in the same processing chamber, a contamination degree is determined previously, which is an index of how a product or the production equipment is contaminated in the production operations; a contamination degree of the product or the production equipment after processing the product in the production operations is set and recorded in a first storage apparatus; a plurality of products having the same contamination degree recorded in the first storage apparatus are grouped into one contamination group; the products are recorded in a second storage apparatus on the basis of the contamination group; and the execution of the processing in the production operations is designated on the basis of the contamination group recorded in the second storage apparatus.

11 Claims, 17 Drawing Sheets

FIG. 6

| Operation | Permissible contamination degree | Contamination degree after processing |
|---|---|---|
| OP1 | 1 | 1 |
| OP2 | 2 | 2 |
| OP3 | 3 | 3 |

FIG. 7

| Dummy run | Contamination state change |
|---|---|
| DR31 | 3→1 |
| DR21 | 2→1 |
| DR32 | 3→2 |

FIG. 8

| Equipment | Operation | Time for processing |
|---|---|---|
| EQ1 | OP1 | TP1 |
| | OP2 | TP2 |
| | OP3 | TP3 |

FIG. 9

| Equipment | Dummy run | Time for processing |
|---|---|---|
| EQ1 | DR31 | TD1 |
| | DR21 | TD2 |
| | DR32 | TD3 |

| Equipment | Lots to be prcoessed | Operation |
|---|---|---|
| EQ1 | WK1 | OP1 |
| | WK2 | OP2 |
| | WK3 | OP3 |
| | WK4 | OP1 |
| | WK5 | OP2 |
| | WK6 | OP3 |
| | WK7 | OP1 |
| | WK8 | OP2 |
| | WK9 | OP3 |

FIG. 10

PRODUCTION MANAGEMENT METHOD

BACKGROUND OF THE INVENTION

1. Field of the Invention

The present invention relates to a production management method for designating a processing order of product processing and dummy runs in a production operation requiring a dummy run for preventing contamination caused by the processing in the course of production.

2. Description of the Related Art

FIG. 20 is a flow chart illustrating processing in a conventional production management method. In FIG. 20, first, lots to be processed are arranged in order of priority (Step S2001). Then, the processing order of the lots to be processed and dummy runs is designated in accordance with the arranged order (Step S2002). Herein, the "dummy run" refers to an indirect operation performed so as to purify a state contaminated by the processing in each operation. Therefore, as the number of dummy runs is increased, an operation that is not directly related to a production operation also is increased, which prolongs the lead time of a lot and increases production costs.

A dummy wafer is used in a dummy run so as to manage a contaminated state in a processing chamber of a production apparatus as follows. First, a dummy wafer is inserted into a production apparatus in the same way as in an ordinary production wafer, and a dummy run is performed. After the dummy run is completed, the dummy wafer is taken out of the production apparatus, and the dummy wafer is measured for a contamination degree by using a measurement apparatus. In the case where the measurement result is determined as a contamination degree at which the subsequent production wafer (lot) can be processed, i.e., cleanness to some degree, the subsequent wafer (lot) is processed Alternatively, in the case where the measurement result is determined as a contamination degree at which the subsequent wafer (lot) cannot be processed, i.e., a contaminated state, a dummy run is performed again without processing the subsequent production wafer (lot). When the second and subsequent dummy runs are performed, the dummy wafer used in the first dummy run may be used, or a new dummy wafer may be used.

In the case where it is determined that contamination can be eliminated to such a desired degree as to satisfy a contamination degree of the subsequent production wafer by performing a dummy run, even when a dummy wafer is used, it is not required to measure a contamination degree of the dummy wafer after the dummy run. In this case, the dummy wafer is used for the purpose of adsorbing a contamination material and enhancing a contamination elimination effect of the dummy run. Therefore, in the case where there is no effect for eliminating the contamination in the dummy run, it is not required to use a dummy wafer.

FIG. 21 shows an example of a processing order of lots to be processed and dummy runs in a conventional production management method. Herein, WK1 to WK9 represent lots to be processed, and TP1 to TP9 represent processing times of the lots WK1 to WK9, respectively. Furthermore, TD3 represents processing time of a dummy run between WK3 and WK2, between WK6 and WK5, and between WK9 and WK8. TD2 represents processing time of a dummy run between WK2 and WK1, between WK5 and WK4, and between WK8 and WK7.

In FIG. 21, it is assumed that the operation for processing WK2 causes more contamination than that of WK1, and the operation for processing WK3 causes more contamination than that of WK2. Furthermore, it is assumed that the operation for processing WK5 causes more contamination than that of WK4, and the operation for processing WK6 causes more contamination than that of WK5. Furthermore, the operation for processing WK8 causes more contamination than that of WK7, and the operation for processing WK9 causes more contamination than that of WK8.

According to the production management method, as shown in FIG. 21, first, the lots to be processed are arranged in order of priority: WK3, WK2, WK1, WK6, WK5, WK4, WK9, WK8, WK7 (Step S2001).

Then, in the processing described below, the processing order of the lots to be processed and the dummy runs is designated in accordance with the arranged order (Step S1402).

Since the operation for processing WK3 causes more contamination than that of WK2, and the operation for processing WK2 causes more contamination than that of WK1, it is necessary to insert dummy runs between WK3 and WK2 and between WK2 and WK1.

Next, since the operation for processing WK6 causes more contamination than that of WK5, and the operation for processing WK4 causes more contamination than that of WK5, it is necessary to insert dummy runs between WK6 and WK5 and between WK5 and WK4.

Furthermore, since the operation for processing WK9 causes more contamination than that of WK8, and the operation for processing WK8 causes more contamination than that of WK7, it is necessary to insert dummy runs between WK9 and WK8 and between WK8 and WK7.

Thus, as an entire processing order, lots and dummy runs are arranged as follows: WK3, dummy run, WK2, dummy run, WK1, WK6, dummy run, WK5, dummy run, WK4, WK9, dummy run, WK8, dummy run, and WK7.

However, according to the above-mentioned production management method, the lots to be processed are arranged merely in order of priority. The lots to be processed are not rearranged considering the contamination degree in each operation. Therefore, 6 dummy runs in total are designated between WK3 and WK2, between WK2 and WK1, between WK6 and WK5, between WK5 and WK4, between WK9 and WK8, and between WK8 and WK7, whereby the total processing time of the dummy runs becomes (total time= TD3+TD2+TD3+TD2+TD3+TD2). This increases the processing number and the processing time of the dummy runs. Consequently, the operating rate of equipment is decreased, and the lead time of a lot is prolonged. Furthermore, an increase in dummy wafer used for dummy runs causes production costs to increase.

SUMMARY OF THE INVENTION

Therefore, with the foregoing in mind, it is an object of the present invention to provide a production management method in which the processing order of lots is designated considering the contamination degree in each operation, whereby the processing number and the processing time of dummy runs can be reduced, the operating rate of equipment can be enhanced, and the lead time of a lot can be shortened, and furthermore, production costs can be reduced by decreasing dummy wafers used in the dummy runs.

In order to achieve the above-mentioned object, a production management method of the present invention includes: in production equipment for performing a plurality of production operations having different processing conditions in the same processing chamber, previously determining a contamination degree that is an index of how a product or the production equipment is contaminated in the production operations, and setting the contamination degree of the product or the production equipment after processing the product in the production operations and recording the contamination degree in one or a plurality of first storage apparatus; grouping a plurality of the products having the same contamination degree recorded in the first storage apparatus into one contamination group and recording the products in one or a plurality of second storage apparatus on the basis of the contamination group; and designating execution of processing in the production operations on the basis of the contamination group recorded in the second storage apparatus.

According to the above configuration, a dummy run only needs to be performed every time the processing of each contamination group is completed. Therefore, the number of dummy runs can be reduced as a whole, and the processing time of the dummy runs can be shortened substantially. This can enhance the operating rate of equipment and shorten the lead time of a lot. Furthermore, production costs can be reduced substantially due to the reduction in the number of dummy wafers to be used.

Furthermore, according to the production management method of the present invention, it is preferable, in a case where the production equipment executes batch processing, one batch process is executed on the basis of the contamination group having the same contamination degree stored in the second storage apparatus.

In order to achieve the above-mentioned object, a production management method of the present invention includes: in production equipment for performing a plurality of production operations having different processing conditions in the same processing chamber, previously determining a contamination degree that is an index of how a product or the production equipment is contaminated in the production operations, and setting the contamination degree of the product or the production equipment after processing the product in the production operations and recording the contamination degree in one or a plurality of first storage apparatus; sorting a plurality of the products in increasing order of the contamination degree recorded in the first storage apparatus, and recording a result in one or a plurality of second storage apparatus; and designating execution of processing in the production operations in accordance with an order of the products recorded in the second storage apparatus.

According to the above configuration, the contamination degree is controlled so as to increase gradually every time the processing of each contamination group is completed. Therefore, a dummy run only needs to be performed once at last, which can minimize the loss of processing time due to the dummy runs. Therefore, the operating rate of equipment can be enhanced and the lead time of a lot can be shortened. Furthermore, production costs can be reduced substantially due to the reduction in the number of dummy wafers to be used.

Furthermore, according to the production management method of the present invention, it is preferable that, in a case where the production equipment adopts a single wafer system, the products are processed successively one by one in accordance with an order of the products recorded in the second storage apparatus.

In order to achieve the above-mentioned object, a production management method of the present invention includes: in production equipment for performing a plurality of production operations having different processing conditions in the same processing chamber, previously determining a contamination degree that is an index of how a product or the production equipment is contaminated in the production operations, and setting the contamination degree of the product or the production equipment after processing the product in the production operations and recording the contamination degree in one or a plurality of first storage apparatus; grouping a plurality of the products having the same contamination degree recorded in the first storage apparatus into one contamination group and recording the products in one or a plurality of second storage apparatus on the basis of the contamination group; sorting a plurality of the products in increasing order of the contamination degree recorded in the second storage apparatus, and recording a result in one or a plurality of third storage apparatus; and designating execution of processing in the production operations in accordance with an order of the products recorded in the third storage apparatus.

According to the above configuration, the contamination degree is controlled so as to increase gradually every time the processing of each contamination group is completed. Therefore, a dummy run only needs to be performed once at last, which can minimize the loss of processing time due to the dummy runs. Therefore, the operating rate of equipment can be enhanced and the lead time of a lot can be shortened. Furthermore, production costs can be reduced substantially due to the reduction in the number of dummy wafers to be used.

Furthermore, according to the production management method of the present invention, it is preferable that, in a case where the production equipment performs batch processing, one batch process is executed on the basis of the contamination group having the same contamination degree stored in the second storage apparatus. It also is preferable that, in a case where the production equipment adopts a single wafer system, the products are processed successively one by one in accordance with an order of the products recorded in the third storage apparatus.

In order to achieve the above-mentioned object, a production management method of the present invention includes: in production equipment for performing a plurality of production operations having different processing conditions in the same processing chamber, previously determining a contamination degree that is an index of how a product or the production equipment is contaminated in the production operations, and setting the contamination degree of the product or the production equipment after processing the product in the production operations and recording the contamination degree in one or a plurality of first storage apparatus; grouping a plurality of the products capable of complying with a delivery date even if an order is changed into one delivery date group, and recording the products in one or a plurality of second storage apparatus on a basis of the delivery date group; sorting the delivery date groups recorded in the second storage apparatus in increasing order of remaining number of days to a delivery date from the delivery date group whose delivery date to be met is earliest, and recording a result in one or a plurality of third storage apparatus; grouping a plurality of the products having the same contamination degree into one contamination group on a basis of the delivery date group, and recording the products in one or a plurality of fourth storage apparatus on the basis of the contamination group; sorting a plurality of the products in increasing order of the contamination degree recorded in the fourth storage apparatus, and recording a result in one or a plurality of fifth storage apparatus; and designating execution of processing in the production operations in accordance with an order of the delivery date groups recorded in the third storage apparatus and an order of the products recorded in the fifth storage apparatus.

According to the above configuration, processing can be executed in increasing order of remaining number of days to a delivery date to be met, and the contamination degree is controlled so as to increase gradually every time the processing of each contamination group is completed. Therefore, a dummy run only needs to be performed once at a time when the processing of each delivery date group is completed, which can minimize the loss of processing time due to the dummy runs. Therefore, the operating rate of equipment can be enhanced and the lead time of a lot can be shortened. Furthermore, production costs can be reduced substantially due to the reduction in the number of dummy wafers to be used.

Furthermore, according to the production management method of the present invention, it is preferable that, in a case where the production equipment performs batch processing, one batch process is executed on the basis of the contamination group having the same contamination degree stored in the fourth storage apparatus. It also is preferable that, in a case where the production equipment adopts a single wafer system, the products are processed successively one by one in accordance with an order of the products recorded in the fifth storage apparatus.

Furthermore, according to the production management method of the present invention, it is preferable that the recording of the products in the second storage apparatus includes: sorting the delivery date groups in increasing order of remaining number of days to a delivery date from the delivery date group whose delivery date to be met is earliest, and recording a result in one or a plurality of sixth storage apparatus; grouping a plurality of the products, which include the product whose delivery date to be met is earliest and are capable of complying with the earliest delivery date to be met even when being replaced by the product whose delivery date to be met is earliest, into a first delivery date group, and recording the products in one or a plurality of seventh storage apparatus on a basis of the first delivery date group; and repeatedly executing further classified grouping based on a delivery date in the same way as in grouping into the first delivery date group among the remaining products that do not belong to the first delivery date group.

According to the above configuration, the delivery date can be managed more accurately, and the contamination degree can be controlled so as to increase gradually every time the processing of each contamination group is completed. Therefore, a dummy run only needs to be performed once at last, which can minimize the loss of processing time due to the dummy runs.

These and other advantages of the present invention will become apparent to those skilled in the art upon reading and understanding the following detailed description with reference to the accompanying figures.

BRIEF DESCRIPTION OF THE DRAWINGS

FIG. 6 shows contamination degree setting information on an operation basis.

FIG. 7 shows contamination change setting information on a dummy run basis.

FIG. 8 shows operation setting information on an equipment basis.

FIG. 9 shows dummy run setting information on an equipment basis.

FIG. 10 shows information on lots to be processed on an equipment basis.

DESCRIPTION OF THE PREFERRED EMBODIMENTS

Hereinafter, various setting conditions in a production management method according to all the following embodiments will be described with reference to FIGS. 5 to 10.

Figure 5:
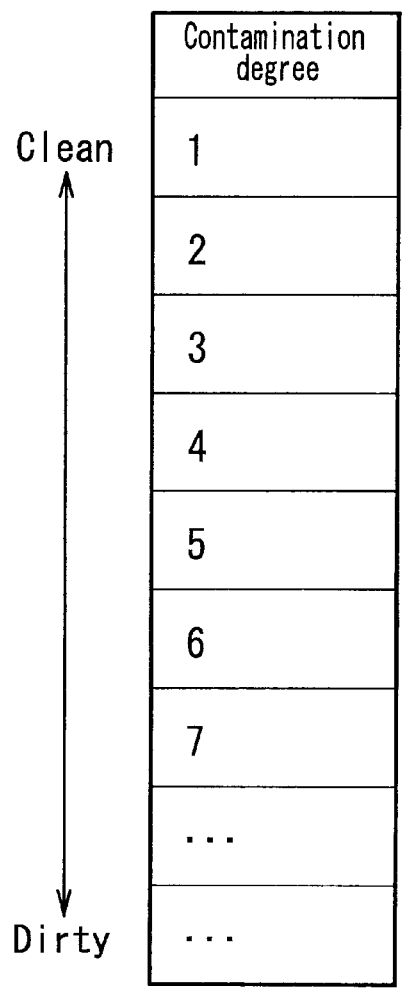
FIG. 5 shows contamination degree definition information.

FIG. 5 illustrates contamination degree definition information in a production management method according to the embodiments of the present invention. As shown in FIG. 5, in all the following embodiments, the contamination degree is represented by the magnitude of a number. It is assumed that '1' represents the cleanest state, and as a number representing a contamination degree is increased, contamination becomes worse. There is no particular limit to a display form of the contamination degree.

FIG. 6 illustrates contamination degree setting information on an operation basis in the production management method according to the embodiments of the present invention. In FIG. 6, a permissible contamination degree represents the dirtiest contamination degree of a product or production equipment permissible in processing a product in an operation. Furthermore, a contamination degree after processing represents a contamination degree of a product or production equipment after processing in an operation. For example, in FIG. 6, it is understood that a permissible contamination degree is '1' and a contamination degree after processing is '1' in an operation OP1, a permissible contamination degree is '2' and a contamination degree after processing is '2' in an operation OP2, and a permissible contamination degree is '3' and a contamination degree after processing is '3' in an operation OP3. Thus, in a range defined in FIG. 6, the operation OP1 is the cleanest operation, the operation OP3 is the dirtiest operation, and the operation OP2 has dirtiness between those of the operations OP1 and OP3.

Next, FIG. 7 illustrates contamination change setting information on a dummy run basis in the production management method according to the embodiments of the present invention. As shown in FIG. 7, in all the following embodiments, the contamination degree changes from '3' to '1' by processing in a dummy run DR31, the contamination degree changes from '3' to '2' by processing in a dummy run DR32, and the contamination degree changes from '2' to '1' by processing in a dummy run DR21.

Furthermore, FIG. 8 illustrates operation setting information on an equipment basis in the production management method according to the embodiments of the present invention. As shown in FIG. 8, in all the following embodiments, for example, equipment EQ1 is set so as to perform processing in the operations OP1, OP2, and OP3. A time for processing in the operation OP1 is represented by TP1, a time for processing in the operation OP2 is represented by TP2, and a time for processing in the operation OP3 is represented by TP3.

Next, FIG. 9 illustrates dummy run setting information on an equipment basis in the production management method according to the embodiments of the present invention. As shown in FIG. 9, in all the following embodiments, for example, equipment EQ1 is set so as to be capable of performing processing in the dummy runs DR31, DR21, and DR32, if required. A time for processing in the dummy run DR31 is represented by TD1, a time for processing in the dummy run DR21 is represented by TD2, and a time for processing in the dummy run DR32 is represented by TD3.

Furthermore, FIG. 10 illustrates information on lots to be processed on an equipment basis in the production management method according to the embodiments of the present invention. As shown in FIG. 10, in all the following embodiments, equipment EQ1 is set to be scheduled for processing lots WK1 to WK9. An operation for processing each lot is as follows: an operation for processing the lot WK1 is represented by OP1, an operation for processing the lot WK2 is represented by OP2, an operation for processing the lot WK3 is represented by OP3, an operation for processing the lot WK4 is represented by OP1, an operation for processing the lot WK5 is represented by OP2, an operation for processing the lot WK6 is represented by OP3, an operation for processing the lot WK7 is represented by OP1, an operation for processing the lot WK8 is represented by OP2, and an operation for processing the lot WK9 is represented by OP3. The order from the lot WK1 to the lot WK9 does not necessarily represent the designated order of lot processing.

Embodiment 1

Figure 1:
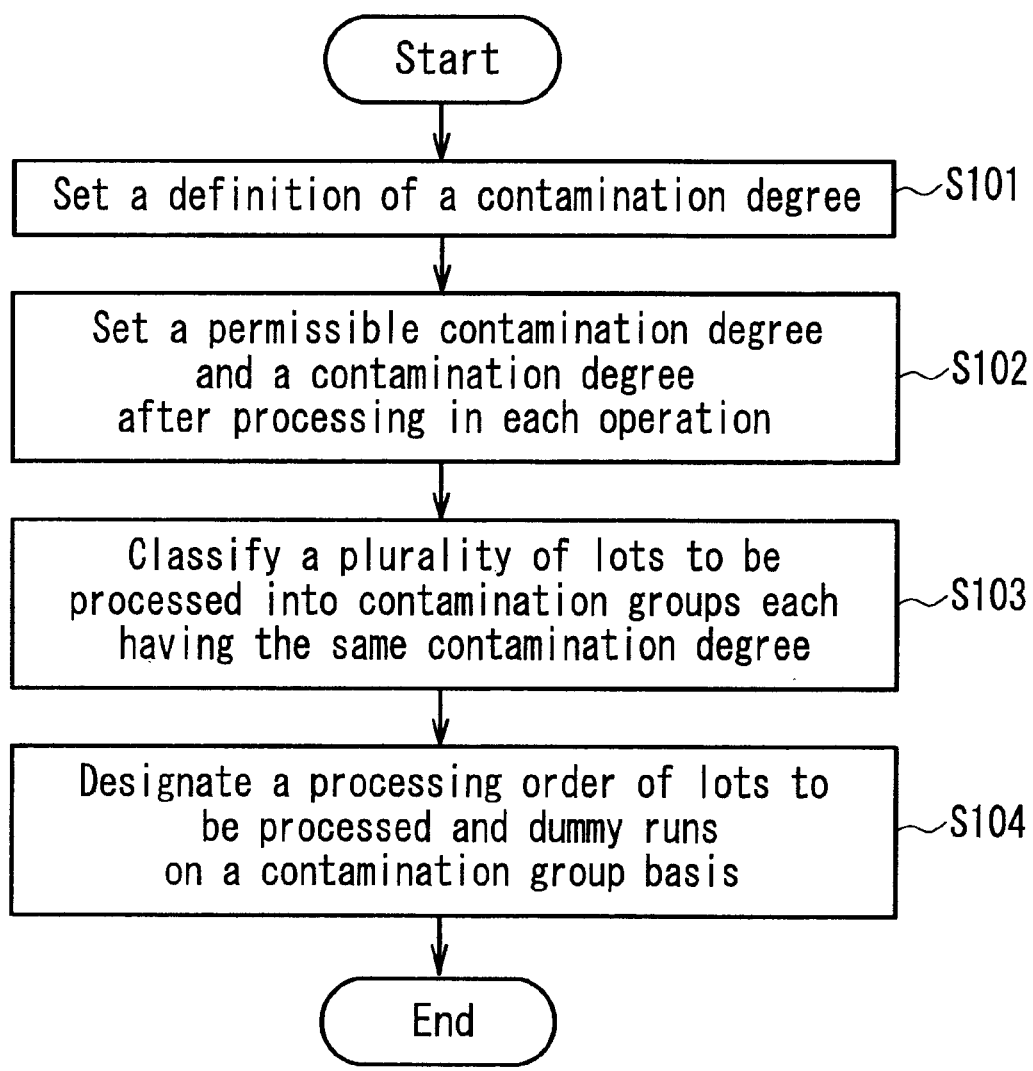
FIG. 1 is a flow chart illustrating processing in a production management method according to Embodiment 1 of the present invention.

Hereinafter, a production management method according to Embodiment 1 of the present invention will be described with reference to the drawings. FIG. 1 is a flow chart illustrating processing in the production management method according to Embodiment 1 of the present invention.

In FIG. 1, first, a definition based on a clear criterion is set with respect to a contamination degree representing how a product or production equipment is contaminated (Step S101). Then, a permissible contamination degree and a contamination degree after processing in a product or production equipment are set on an operation basis (Step S102). For example, as shown in FIGS. 5 and 6, the permissible contamination degree and the contamination degree after processing are set specifically on a processing operation basis. The permissible contamination degree and the contamination degree after processing may be set with respect to a product or they may be set with respect to production equipment.

Next, a plurality of lots to be processed are classified into contamination groups each having the same contamination degree after processing (Step S103). The processing order of the lots to be processed is designated on a contamination group basis (Step S104).

More specifically, the case where production equipment EQ1 is scheduled for processing lots WK1 to WK9 will be described based on the setting conditions shown in FIGS. 5 to 10.

First, as shown in FIG. 10, the respective lots WK1 to WK9 are processed in either of the operations OP1 to OP3. Furthermore, as shown in FIG. 8, times for processing in the operations OP1, OP2, and OP3 are TP1, TP2, and TP3, respectively. Furthermore, as shown in FIG. 7, three dummy runs are defined as follows: DR31 for allowing the contamination degree to change from '3' to '1' in the case of performing the operation OP1 after the operation OP3; DR32 for allowing the contamination degree to change from '2' to '1' in the case of performing the operation OP1 after the operation OP2; and DR3 for allowing the contamination degree to change from '3' to '2' in the case of performing the operation OP2 after the operation OP3. Furthermore, as shown in FIG. 9, times for processing in the dummy runs DR1, DR2, and DR3 are TD1, TD2, and TD3, respectively.

For example, it is assumed that the lots WK1 to WK9 are rearranged in the order of WK3, WK2, WK1, WK6, WK5, WK4, WK9, WK8, and WK7 based on priority as in a conventional example.

Figure 11:
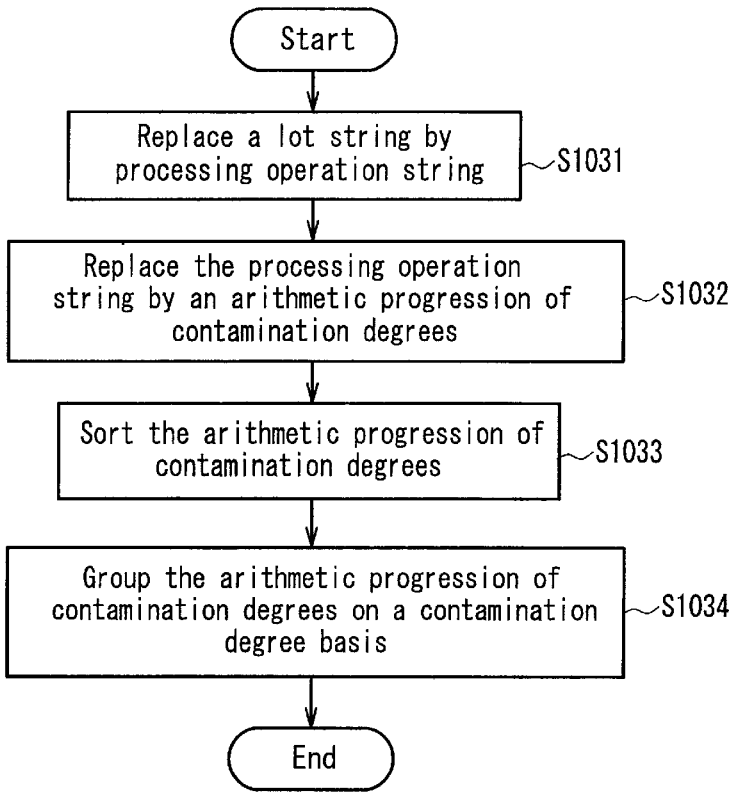
FIG. 11 is a flow chart illustrating contamination group classification processing in the production management method according to Embodiment 1 of the present invention.

The processing of classifying a plurality of lots to be processed into contamination groups each having the same contamination degree in Step S103 is performed, for example, as shown in FIG. 11. FIG. 11 is a flow chart illustrating the processing in Step S103.

In FIG. 11, first, the lots WK3, WK2, WK1, WK6, WK5, WK4, WK9, WK8, and WK7 are replaced by the operations for processing them, using the information on lots to be processed on an equipment basis shown in FIG. 10, as follows: OP3, OP2, OP1, OP3, OP2, OP1, OP3, OP2, and OP1 (Step S1031).

Then, the operations OP3, OP2, OP1, OP3, OP2, OP1, OP3, OP2, and OP1 are replaced by contamination degrees after the processing in each operation, using the contamination degree setting information on an operation basis shown in FIG. 6, as follows: 3, 2, 1, 3, 2, 1, 3, 2, and 1 (Step S1032).

The arithmetic progression of contamination degrees thus obtained is arranged in decreasing order by various sort algorithms (e.g., bubble sort, selection sort, insertion sort, shell sort, quick sort, heap sort, merge sort, and the like), for example, as follows: 3, 3, 3, 2, 2, 2, 1, 1, and 1 (Step S1033).

Next, the arithmetic progression with the same contamination degree is grouped (Step S1034). More specifically, a contamination group with a contamination degree of '3' is set to be PG3, a contamination group with a contamination degree of '2' is set to be PG2, and a contamination group with a contamination degree of '1' is set to be PG1, whereby the arithmetic progression of contamination degrees can be replaced by the contamination group string: PG3, PG2, and PG1.

Figure 12:
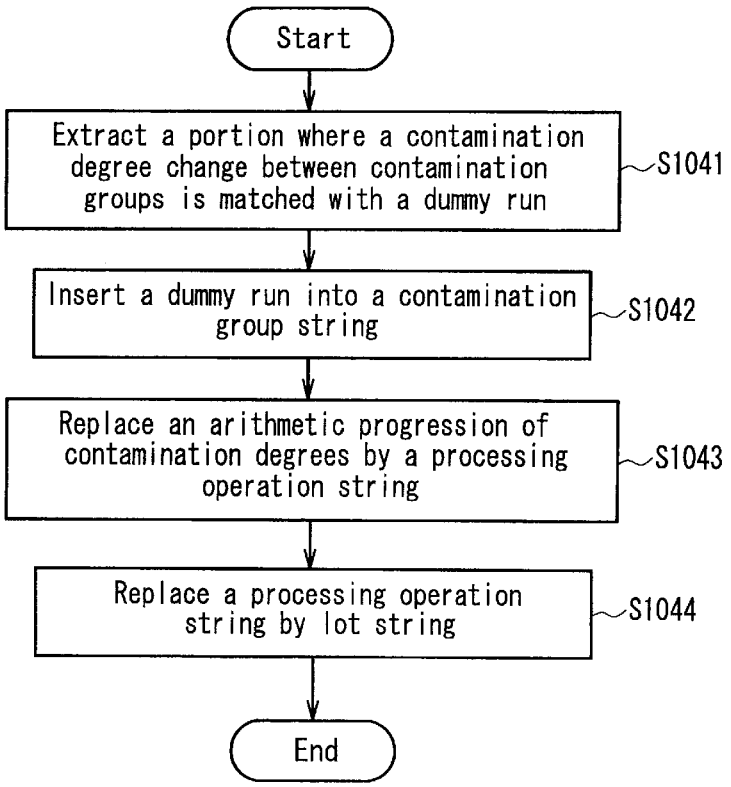
FIG. 12 is a flow chart illustrating processing of designating a processing order in the production management method according to Embodiment 1 of the present invention.

Furthermore, the processing of designating a processing order of lots to be processed and dummy runs on a contamination group basis in Step S104 is performed specifically as shown in FIG. 12. FIG. 12 is a flow chart illustrating the processing in Step S104.

In FIG. 12, a portion where the contamination degree change between contamination groups is (3→2) and a portion where the contamination degree change between contamination groups is (2→1) are searched for and extracted (Step S1041).

Next, using the contamination change setting information on a dummy run basis shown in FIG. 7, dummy runs allowing the contamination degree to change corresponding to the contamination degree change searched for and extracted are inserted into the contamination group string. In Embodiment 1, the contamination group string of PG3, DR32, PG2, DR21, and PG1 is obtained, and returned to the arithmetic progression of contamination degrees as follows: 3, 3, 3, DR32, 2, 2, 2, DR21, 1, 1, and 1 (Step S1042).

Next, the arithmetic progression of contamination degrees are replaced by corresponding processing operations, using the contamination degree setting information on an operation basis shown in FIG. 6, as follows: OP3, OP3, OP3, DR32, OP2, OP2, OP2, DR21, OP1, OP1, and OP1 (Step S1043).

Finally, the operations OP3, OP3, OP3, DR32, OP2, OP2, OP2, DR21, OP1, OP1, and OP1 are replaced, using the information on lots to be processed on an equipment basis shown in FIG. 10, for example, as follows: WK3, WK6, WK9, DR32, WK2, WK5, WK8, DR21, WK1, WK4, and WK7 (Step S1044).

Figure 13A:
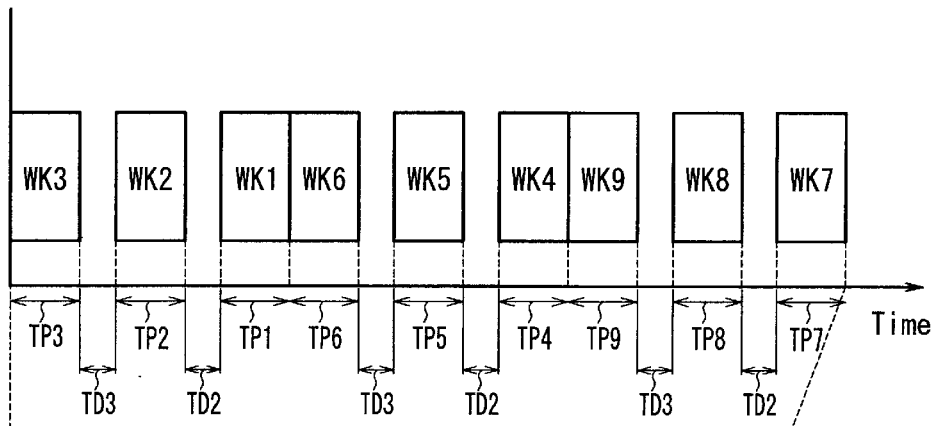
FIGS. 13A and 13B are time charts designating a lot processing order in the production management method according to Embodiment 1 of the present invention.
Figure 13B:
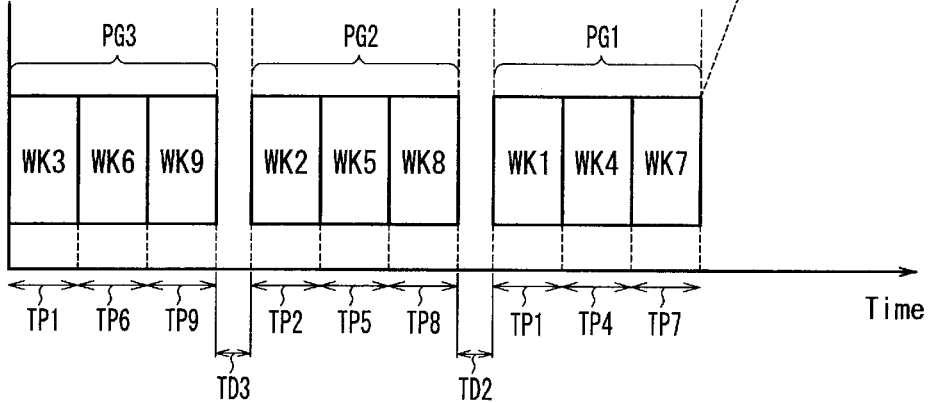

FIGS. 13A and 13B show an arrangement of lot processing and dummy runs in a time chart. FIG. 13B shows the obtained time chart, and FIG. 13A shows a conventional time chart on the same scale as that of FIG. 13B for comparison.

In FIG. 13B, the lot processing is designated in the order of the lots WK3, WK6, and WK9 in the operation OP3 with a contamination degree of '3'; the lot processing is designated in the order of the lots WK2, WK5, and WK8 in the operation OP2 with a contamination degree of '2'; the lot processing is designated in the order of the lots WK1, WK4, and WK7 in the operation OP1 with a contamination degree of '1'; a dummy run DR32 is designated between WK9 and WK2; and a dummy run DR21 is designated between WK8 and WK1. Therefore, it is understood that compared with FIG. 13A, the number of dummy runs is decreased from 6 to 2. Furthermore, the time for performing dummy runs is decreased from (TD3+TD2+TD3+TD2+TD3+TD2) to (TD3+TD2).

As described above, according to Embodiment 1 of the present invention, the operating rate of equipment can be enhanced, and the lead time of the entire lots can be shortened. In addition, the number of dummy wafers to be used can be reduced (to ⅓ in Embodiment 1). This enables the production costs to be reduced.

Embodiment 2

Figure 2:
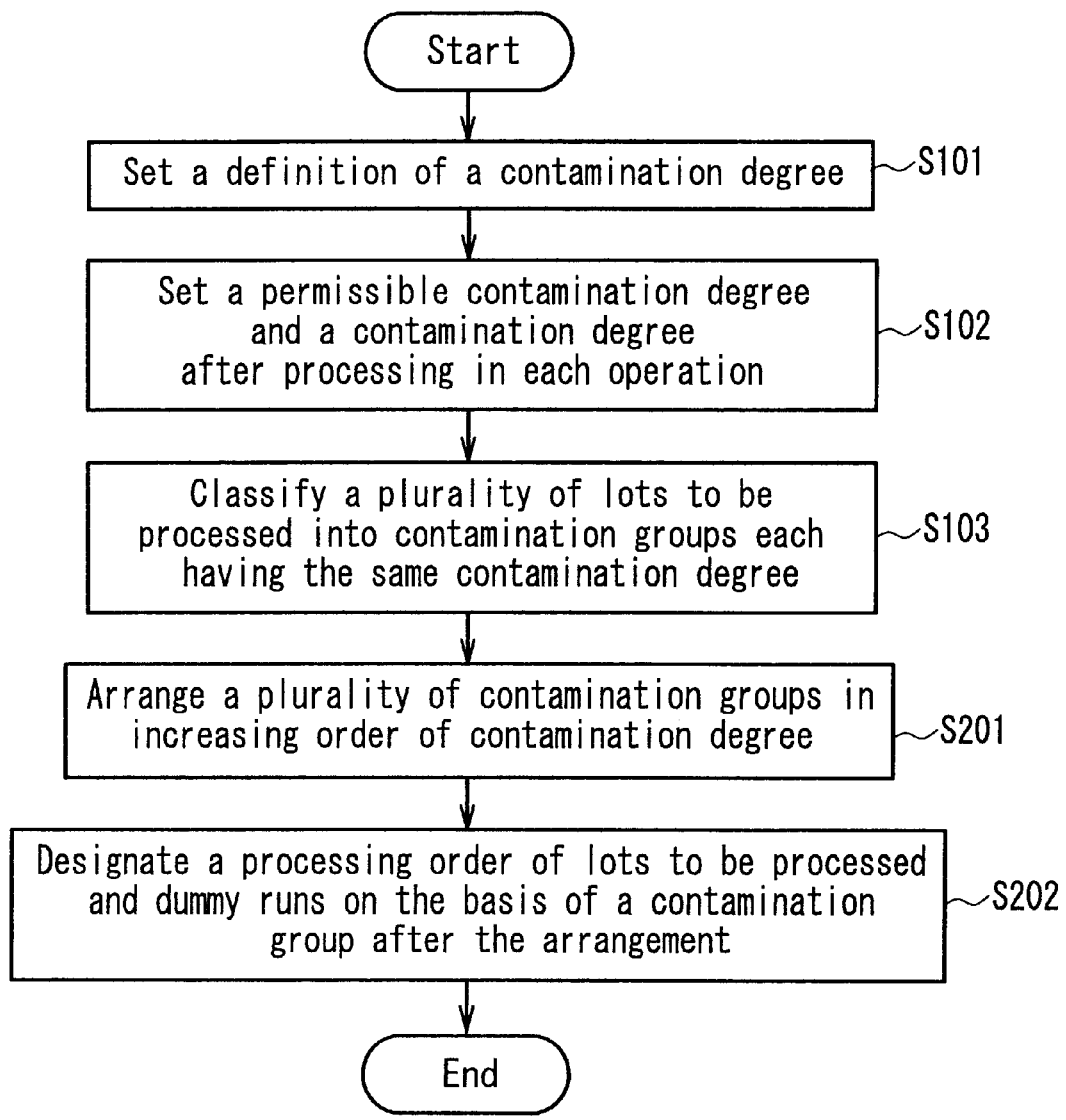
FIG. 2 is a flow chart illustrating processing in a production management method according to Embodiment 2 of the present invention.

Hereinafter, a production management method according to Embodiment 2 of the present invention will be described with reference to the drawings. FIG. 2 is a flow chart illustrating processing in the production management method according to Embodiment 2 of the present invention.

In FIG. 2, first, a definition based on a clear criterion is set with respect to a contamination degree representing how a product or production equipment is contaminated in the same way as in Embodiment 1 (Step S101). Then, a permissible contamination degree and a contamination degree after processing in a product or production equipment are set on an operation basis (Step S102). The permissible contamination degree and the contamination degree after processing may be set with respect to a product or they may be set with respect to production equipment in the same way as in Embodiment 1. Then, a plurality of lots to be processed are classified into contamination groups each having the same contamination degree (Step S103).

Next, the contamination groups are arranged in increasing order of contamination degree from a contamination group with the lowest contamination degree (Step S201). The processing order of lots to be processed and dummy runs is designated in accordance with the order of the contamination groups after the arrangement (Step S202).

More specifically, in the same way as in Embodiment 1, the case where production equipment EQ1 is scheduled for processing lots WK1 to WK9 will be described based on the setting conditions shown in FIGS. 5 to 10.

First, for example, it is assumed that the lots WK1 to WK9 are rearranged in the order of WK3, WK2, WK1, WK6, WK5, WK4, WK9, WK8, and WK7 based on priority as in a conventional example.

The processing of classifying a plurality of lots to be processed into contamination groups each having the same contamination degree in Step S103 is performed in the same way as in Embodiment 1 shown in FIG. 11.

Figure 14:
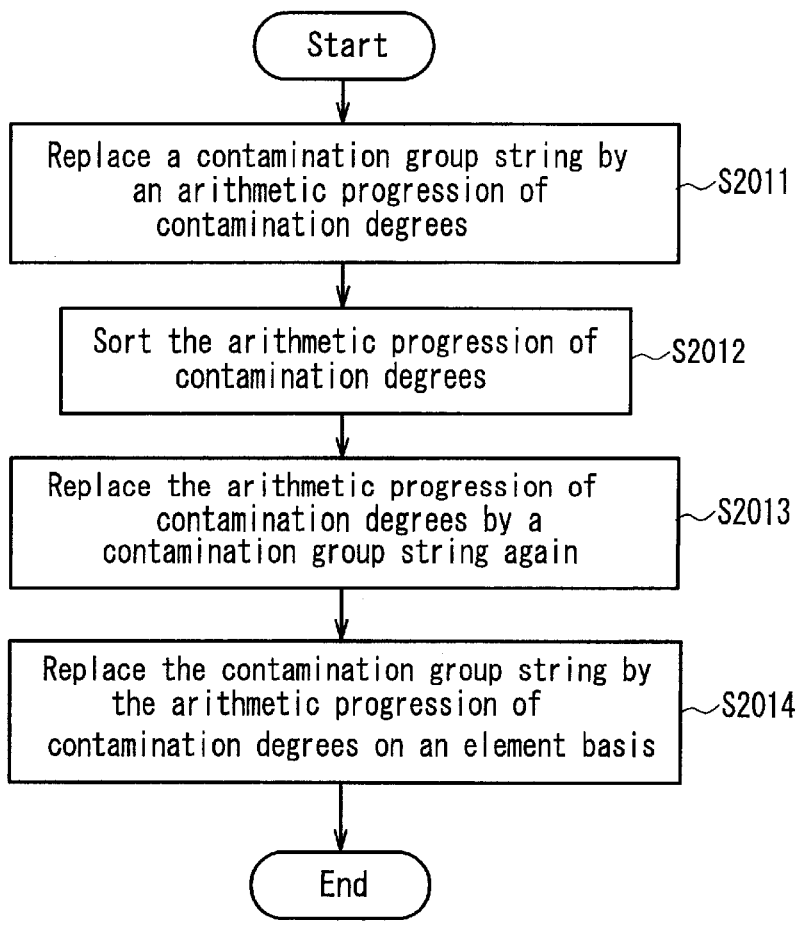
FIG. 14 is a flow chart illustrating contamination group arrangement processing in the production management method according to Embodiment 2 of the present invention.

Furthermore, the processing of arranging a plurality of contamination groups in increasing order of contamination degree from a contamination group with the lowest contamination degree in Step S201 is performed specifically as shown in FIG. 14. FIG. 14 is a flow chart illustrating the processing in Step S201.

In FIG. 14, first, the contamination groups PG3, PG2, and PG1 are replaced by contamination degrees as follows: 3, 2, and 1 (Step S2011).

Next, the arithmetic progression of contamination degrees is arranged by various sort algorithms (e.g., bubble sort, selection sort, insertion sort, shell sort, quick sort, heap sort, merge sort, and the like), for example, as follows: 1, 2, and 3 (Step S2012).

The arithmetic progression of contamination degrees is replaced by the contamination group string again as follows: PG1, PG2, and PG3 (Step S2013). Thereafter, the contamination group string is replaced by the arithmetic progression of contamination degrees as follows: 1, 1, 1, 2, 2, 2, 3, 3, and 3 (Step S2014).

Figure 15:
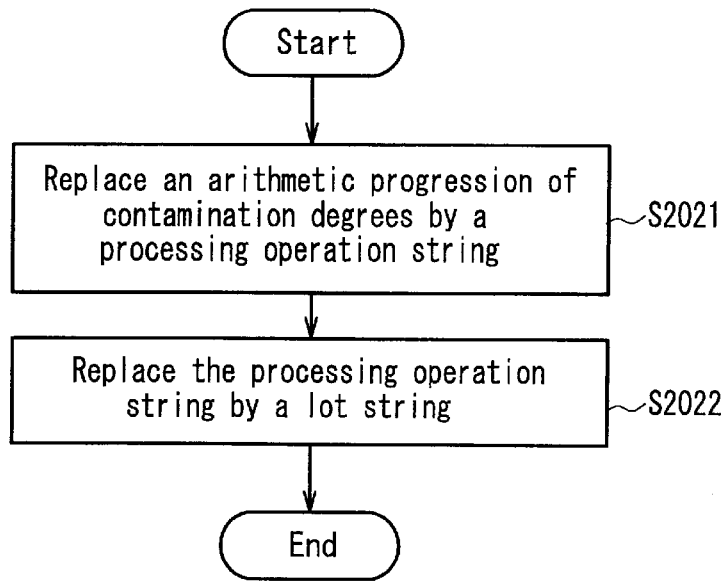
FIG. 15 is a flow chart illustrating processing of designating a processing order in the production management method according to Embodiment 2 of the present invention.

Next, the processing of designating a processing order of lots to be processed and dummy runs in accordance with the order of contamination groups after the arrangement in Step S202 is performed specifically as shown in FIG. 15. FIG. 15 is a flow chart illustrating the processing in Step S202.

First, the arithmetic progression of contamination degrees is replaced by operations, using the contamination degree setting information shown in FIG. 6 as follows: OP1, OP1, OP1, OP2, OP2, OP2, OP3, OP3, and OP3 (Step S2021)

Next, the operations OP1, OP1, OP1, OP2, OP2, OP2, OP3, OP3, and OP3 are replaced, using the information on lots to be processed on an equipment basis shown in FIG. 10, for example, as follows: WK1, WK4, WK7, WK2, WK5, WK8, WK3, WK6, and WK9 (Step S2022). This case is characterized in that the dummy runs are not required at all.

Figure 16A:
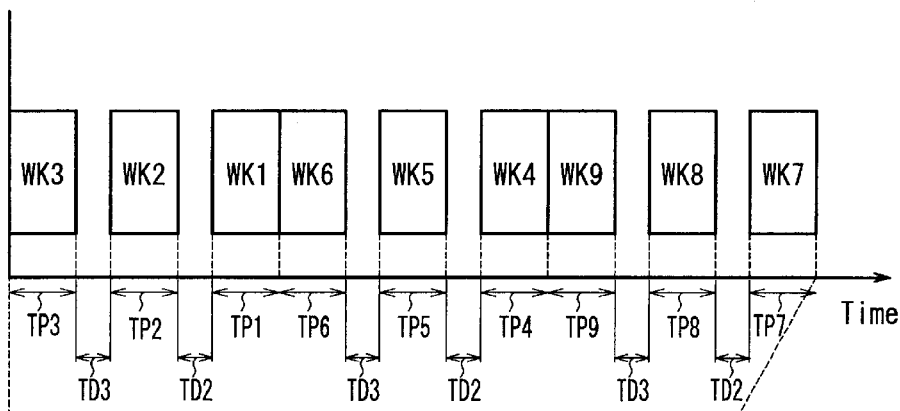
FIGS. 16A and 16B are time charts designating a lot processing order in the production management method according to Embodiment 2 of the present invention.
Figure 16B:
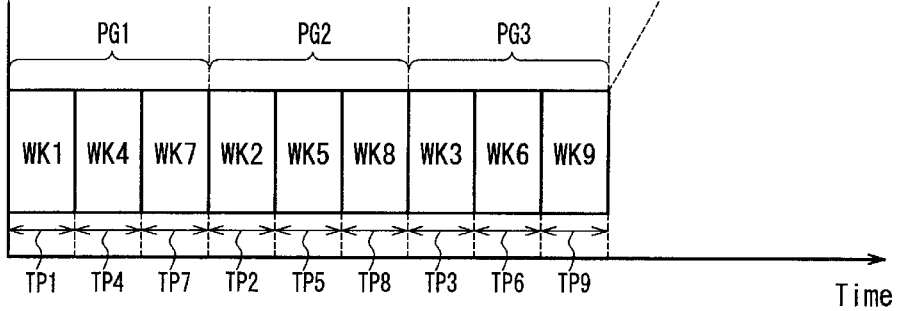

FIGS. 16A and 16B show an arrangement of the above-mentioned lot processing in a time chart. FIG. 16B shows the obtained time chart, and FIG. 16A shows a conventional time chart on the same scale as that of FIG. 16B for comparison.

In FIG. 16B, the lot processing is designated in the order of the lots WK1, WK4, and WK7 in the operation OP1 with a contamination degree of '1'; the lot processing is designated in the order of the lots WK2, WK5, and WK8 in the operation OP2 with a contamination degree of '2'; and the lot processing is designated in the order of the lots WK3, WK6, and WK9 in the operation OP3 with a contamination degree of '3'. Therefore, it is understood that the number of dummy runs is decreased from 6 to 0. Furthermore, the time for performing dummy runs is decreased from (TD3+TD2+TD3+TD2+TD3+TD2) to 0.

As described above, according to Embodiment 2 of the present invention, the operating rate of equipment can be enhanced, and the lead time of the entire lots can be shortened substantially. In addition, no dummy wafers are required. This enables the production costs to be reduced substantially.

In Embodiment 2, processing operations are grouped as contamination groups, and the contamination groups are rearranged in increasing order from a contamination group with the lowest contamination degree. However, even when the processing operations are rearranged in increasing order of contamination degree after processing in a production operation, without grouping them as contamination groups, the same effects can be expected.

Embodiment 3

Figure 3:
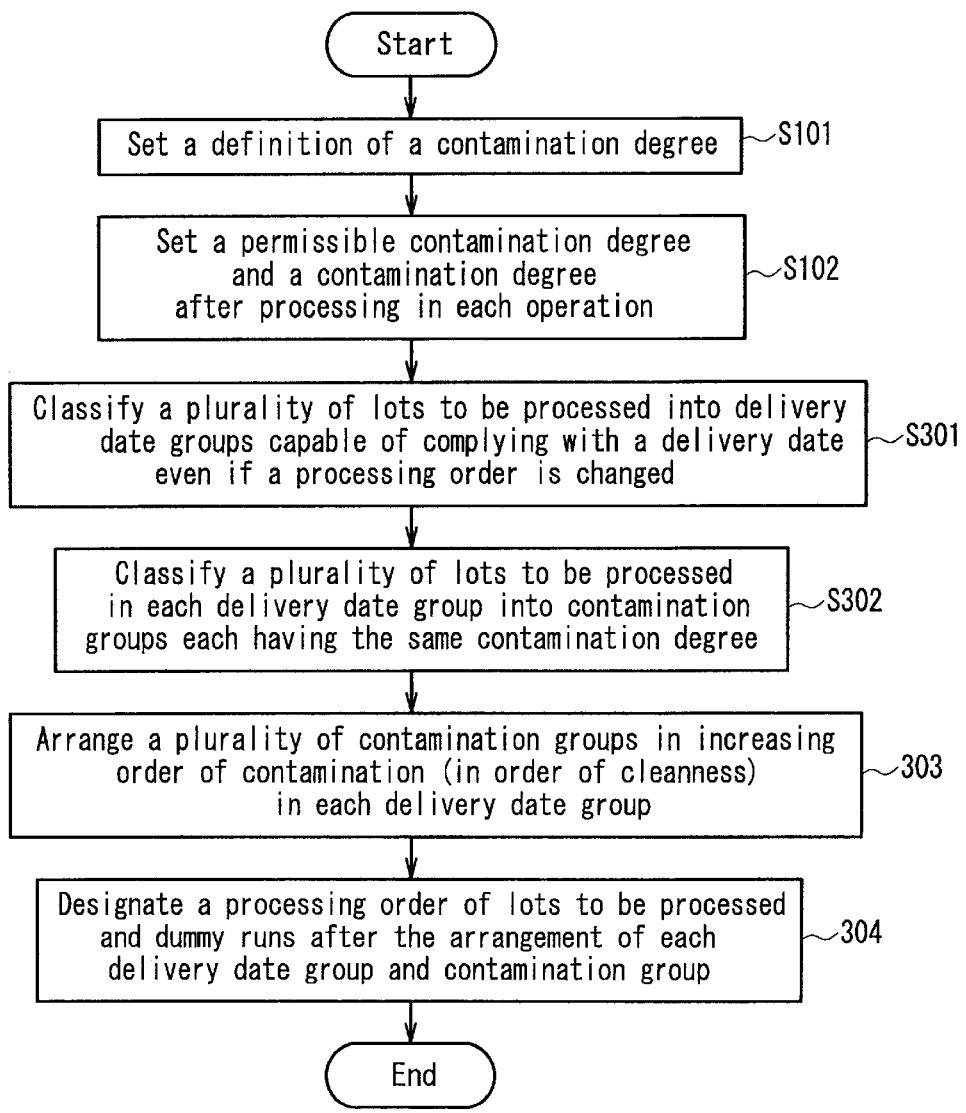
FIG. 3 is a flow chart illustrating processing in a production management method according to Embodiment 3 of the present invention.

Hereinafter, a production management method according to Embodiment 3 of the present invention will be described with reference to the drawings. FIG. 3 is a flow chart illustrating processing in the production management method according to Embodiment 3 of the present invention.

In FIG. 3, in the same way as in Embodiment 1, first, a definition based on a clear criterion is set with respect to a contamination degree representing how a product or production equipment is contaminated (Step S101). Then, a permissible contamination degree and a contamination degree after processing in a product or production equipment are set on an operation basis (Step S102). In the same way as in Embodiment 1, the permissible contamination degree and the contamination degree after processing may be set with respect to a product or they may be set with respect to production equipment.

Next, a plurality of lots to be processed are classified into delivery date groups capable of complying with the delivery date even if a processing order is changed (Step S301) A plurality of lots to be processed in each delivery date group are classified into contamination groups each having the same contamination degree (Step S302). Then, in each delivery date group, the contamination groups are arranged in increasing order of contamination degree in the same way as in Embodiment 2 (Step S303). After the arrangement of each delivery date group and contamination group, the processing order of the lots to be processed and dummy runs is designated (Step S304).

Figure 4:
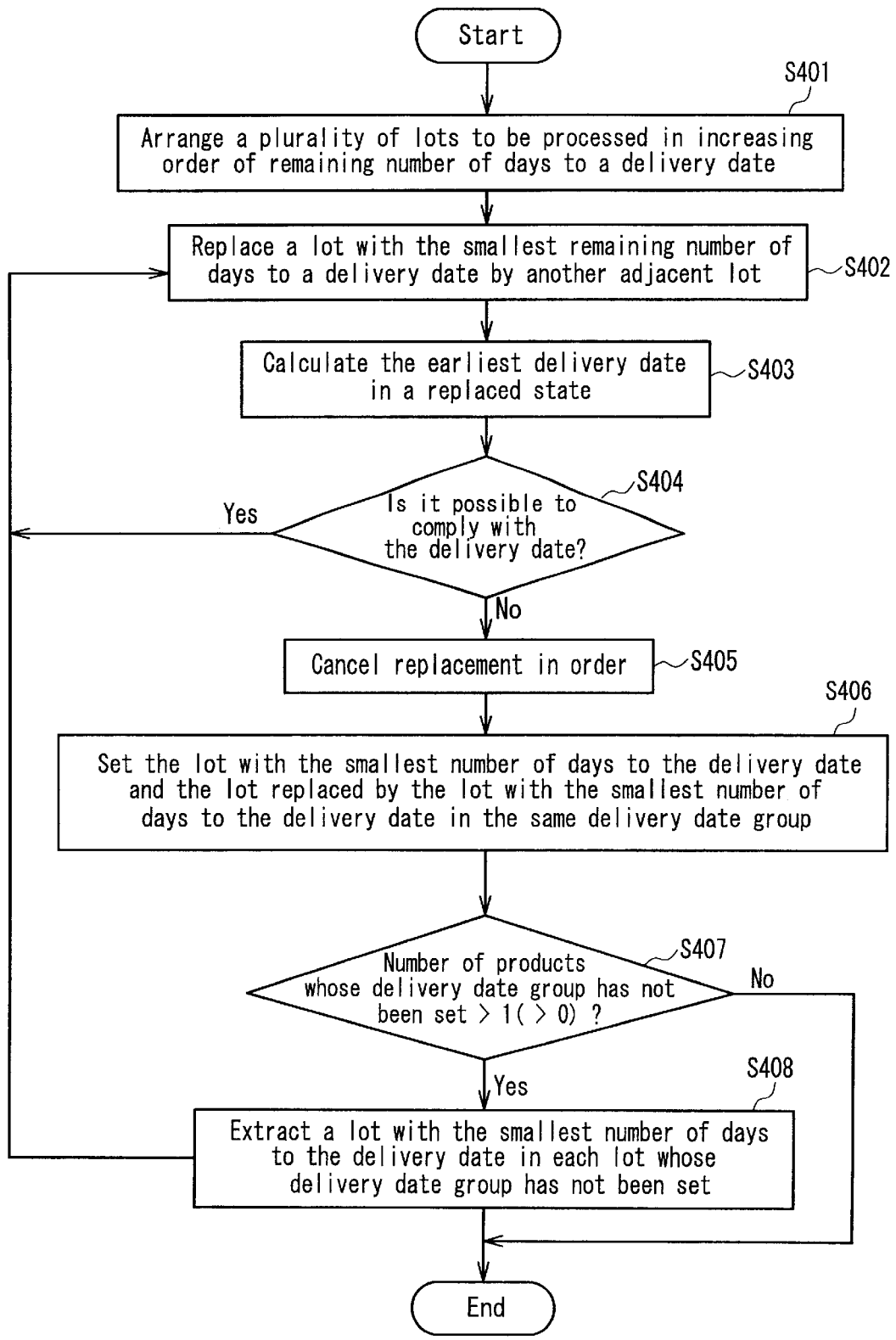
FIG. 4 is a flow chart illustrating delivery date group setting processing in the production management method according to Embodiment 3 of the present invention.

Furthermore, in Step S301, as shown in FIG. 4, a plurality of lots to be processed are arranged in increasing order of remaining number of days to the delivery date (Step S401). A lot with the smallest remaining number of days to the delivery date is replaced by an adjacent lot (Step S402). The earliest delivery date in the replaced state is calculated (Step S403). It is determined whether or not the lot with the smallest remaining number of days to the delivery date can comply with the delivery date (Step S404).

Then, a lot with the smallest remaining number of days to the delivery date is replaced by an adjacent lot repeatedly until it is determined that the lot with the smallest remaining number of days to the delivery date cannot comply with the delivery date. In the case where it is determined that the lot with the smallest remaining number of days to the delivery date cannot comply with the delivery date (Step S404: No), only replacement by the last adjacent lot is cancelled (Step S405).

The lot with the smallest remaining number of days to the delivery date and the lot replaced by the lot with the smallest remaining number of days to the delivery date are set in the same delivery date group (Step S406), and the number of lots whose delivery date group has not been set is checked (Step S407).

In the case where the number of lots whose delivery date group has not been set is larger than '1' (Step S407: Yes), the lot with the smallest remaining number of days to the delivery date among the lots whose delivery date group has not been set is set as a lot with the smallest remaining number of days to the delivery date (Step S408), and the above-mentioned processing of grouping lots into a delivery date group is repeated. More specifically, in the same way as in Embodiment 1, the case where production equipment EQ1 is scheduled for processing the lots WK1 to WK9 will be described based on the setting conditions illustrated in FIGS. 5 to 10.

First, in the processing of classifying a plurality of lots to be processed into delivery date groups capable of complying with the delivery date even when a processing order is changed in Step S301, as shown in FIG. 4, first, the lots WK1 to WK9 are rearranged in increasing order of remaining number of days as follows: WK3, WK2, WK1, WK6, WK5, WK4, WK9, WK8, and WK7 (Step S401).

Next, the lot WK3 with the smallest remaining number of days to the delivery date is replaced by the other lots WK2, WK1, WK6, WK5, WK4, WK9, WK8, and WK7 (Step S402). By using, for example, a production simulator or the like in each case, the earliest delivery date in each replaced case is calculated (Step S403).

Herein, for example, the following is assumed: when the lot WK3 is replaced by the lots WK2, WK1, and WK6, the calculated delivery date is the same as that determined by the lot WK3, and when the lot WK3 is replaced by the lots WK2, WK1, WK6, and WK5, the calculated delivery date exceeds the delivery date determined by the lot WK3 (Step S404). In this case, a delivery date group OG1 including the lot WK3 is composed of the lots WK3, WK2, WK1, and WK6 (Steps S405 and S406).

Next, the number of lots that do not belong to the delivery date group OG1 is calculated (Step S407). Herein, the total number of the lots WK5, WK4, WK9, WK8, and WK7 is '5', so that 5>1.

Then, a lot with the smallest remaining number of days to the delivery date is searched for among those which exclude the lots WK3, WK2, WK1, and WK6 belonging to the delivery date group OG1 (Step S408). Herein, it is assumed that the lot WK5 has the smallest remaining number of days to the delivery date.

Next, the lot WK5 with the smallest remaining number of days to the delivery date is replaced by the other lots WK4, WK9, WK8, and WK7 whose delivery date group has not been set (Step S402). By using, for example, a production simulator or the like in each case, the earliest delivery date in each replaced case is calculated (Step S403).

Herein, for example, the following is assumed: when the lot WK5 is replaced by the lots WK4 and WK9, the calculated delivery date is the same as that determined by the lot WK5. When the lot WK5 is replaced by the lots WK4, WK9, and WK8, the calculated delivery date exceeds the delivery date determined by the lot WK5 (Step S404). In this case, a delivery date group OG2 including the lot WK5 is composed of the lots WK5, WK4, and WK9 (Steps S405 and S406).

Next, the number of lots that do not belong to the delivery date groups OG1 and OG2 is calculated (Step S407). Herein, the total number of lots WK8 and WK7 is '2', so that 2>1.

Then, a lot with the smallest remaining number of days to the delivery date is searched for among those which exclude the lots WK3, WK2, WK1, WK6, WK5, WK4, and WK9 belonging to the delivery date groups OG1 and OG2 (Step S408). Herein, it is assumed that the lot WK8 has the smallest remaining number of days to the delivery date.

Next, the lot WK8 is replaced by the lot WK7 whose delivery date group has not been set, and by using, for example, a production simulator or the like in each case, the earliest delivery date in each replaced case is calculated (Step S403).

Herein, for example, it is assumed that when the lot WK8 is replaced by the lot WK7, the calculated delivery date is the same as that determined by the lot WK8 (Step S404). In this case, a delivery date group OG3 including the lot WK8 is composed of the lots WK8 and WK7 (Steps S405 and S406).

Next, the number of lots that do not belong to the delivery date groups OG1, OG2, and OG3 is calculated (Step S408). Herein, the total number of lots is '0', so that 0<1.

By performing the above processing, the lots are grouped into three delivery date groups: the delivery date group OG1 composed of the lots WK3, WK2, WK1, and WK6; the delivery date group OG2 composed of the lots WK5, WK4, and WK9; and the delivery date group OG3 composed of the lots WK8 and WK7.

Next, the lots are classified into contamination groups on a delivery date group basis, and arranged in increasing order of contamination degree (Steps S302 and S303).

Specifically, the lots WK3, WK2, WK1, and WK6 in the delivery date group OG1 are replaced by the operations for processing them, based on the information on lots to be processed on an equipment basis shown in FIG. 10, as follows: OP3, OP2, OP1, and OP3. Then, the operations OP3, OP2, OP1, and OP3 are replaced by the contamination degrees, based on the contamination degree setting information on an operation basis shown in FIG. 6, as follows: 3, 2, 1, and 3.

Next, the arithmetic progression of contamination degrees thus obtained is arranged by various sort algorithms (e.g., bubble sort, selection sort, insertion sort, shell sort, quick sort, heap sort, merge sort, and the like), for example, as follows: 3, 3, 2, and 1.

Next, the arithmetic progression with the same contamination degree is grouped. That is, it is assumed that the contamination group with a contamination degree of '3' is PG3, the contamination group with a contamination degree of '2' is PG2, and the contamination group with a contamination degree of '1' is PG1. Then, by replacing the contamination groups PG3, PG2, and PG1 by contamination degrees, the arithmetic progression of contamination degrees: 3, 2, and 1 is obtained.

Then, the arithmetic progression of contamination degrees thus obtained is arranged by various sort algorithms (e.g., bubble sort, selection sort, insertion sort, shell sort, quick sort, heap sort, merge sort, and the like), for example, as follows: 1, 2, and 3. Then, by replacing the arithmetic progression of contamination degrees by contamination groups, a contamination group string: PG1, PG2, and PG3 is obtained.

The contamination group string thus obtained is replaced again by the arithmetic progression of contamination degrees with respect to the lots in the delivery date group OG1 as follows: 1, 2, 3, and 3. The arithmetic progression of contamination degrees is replaced by operations, based on the contamination degree setting information on an operation basis shown in FIG. 6, as follows: OP1, OP2, OP3, and OP3.

Next, the operations OP1, OP2, OP3, and OP3 are replaced by lots based on the information on lots to be processed on an equipment basis shown in FIG. 10, for example, as follows: WK1, WK2, WK3, and WK6.

Similarly, the delivery date group OG2 is classified into contamination groups, and the contamination groups are arranged in increasing order of contamination degree (Steps S302 and S303). Herein, the arrangement of WK4, WK5, and WK9 is obtained.

Similarly, the delivery date group OG3 is classified into contamination groups, and the contamination groups are arranged in increasing order of contamination degree (Steps S302 and S303). Herein, the arrangement of WK7 and WK8 is obtained.

After the arrangement of each delivery date group and contamination group is completed, the processing order of lots to be processed and dummy runs is designated (Step S304). The processing thereof is performed specifically as shown in FIG. 17.

Figure 17:
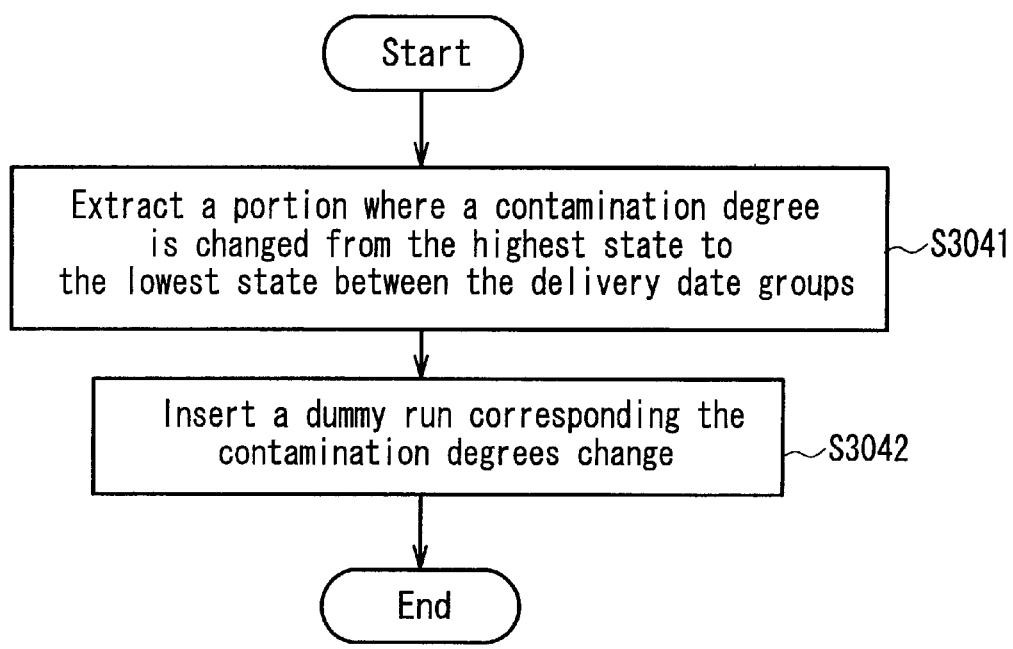
FIG. 17 is a flow chart illustrating the processing of designating a processing order in the production management method according to Embodiment 3 of the present invention.

In FIG. 17, a portion where the contamination degree change between the delivery date groups is (3→1) is searched for (Step S3041).

Then, a dummy run allowing the contamination degree to change in the same way as in the above is inserted into the contamination group string. Herein, the arrangement of OG3, DR31, OG2, DR31, and OG1, i.e., the arrangement of WK1, WK2, WK3, WK6, DR31, WK4, WK5, WK9, DR31, WK7, and WK8 is obtained (Step S3042).

Figure 18A:
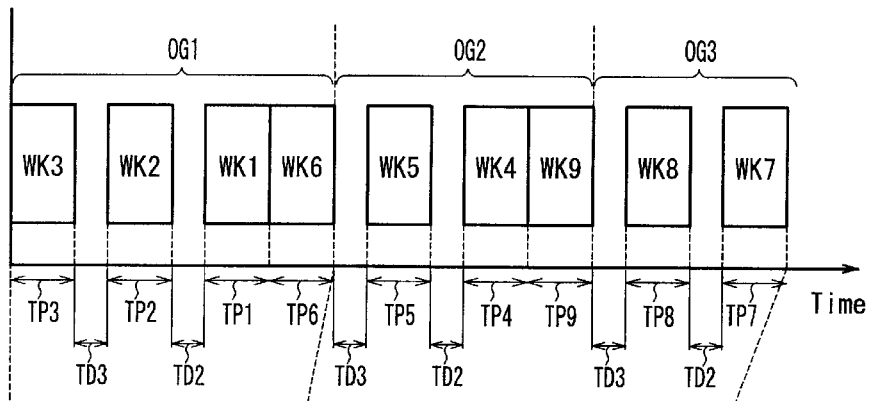
FIGS. 18A and 18B are time charts designating a lot processing order in the production management method according to Embodiment 3 of the present invention.
Figure 18B:
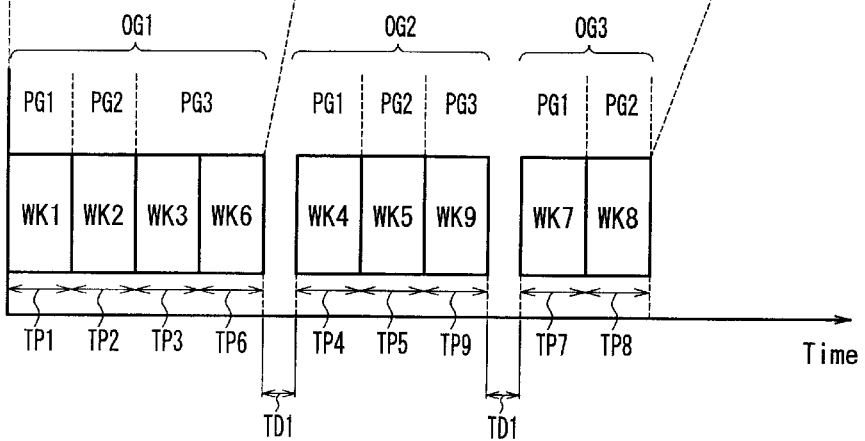

FIGS. 18A and 18B show an arrangement of lot processing and dummy runs in a time chart. FIG. 18B shows the obtained time chart, and FIG. 18A shows a conventional time chart on the same scale as that of FIG. 18B for comparison.

In FIG. 18B, the lot processing is designated in the following order: the delivery date group OG1 (lots WK1, WK2, WK3, and WK6), the dummy run DR31, the delivery date group OG2 (lots WK4, WK5, and WK9), the dummy run DR31, and the delivery date group OG3 (lots WK7 and WK8). Therefore, it is understood that compared with FIG. 13A, the number of dummy runs is decreased from 6 to 2. Furthermore, the time for performing dummy runs is decreased from (TD3+TD2+TD3+TD2+TD3+TD2) to (TD1+TD1).

As described above, according to Embodiment 3 of the present invention, the operating rate of equipment can be enhanced, and the lead time of the entire lots can be shortened. In addition, the number of dummy wafers to be used can be reduced (to ⅓ in Embodiment 3). This enables production costs to be reduced.

In Embodiment 3, the remaining number of days to the delivery date is used as the urgency with respect to the delivery date. However, the index of urgency such as the ratio between the remaining number of days and the remaining number of operations may be used, which corresponds to the operation of a production line.

Figure 19:
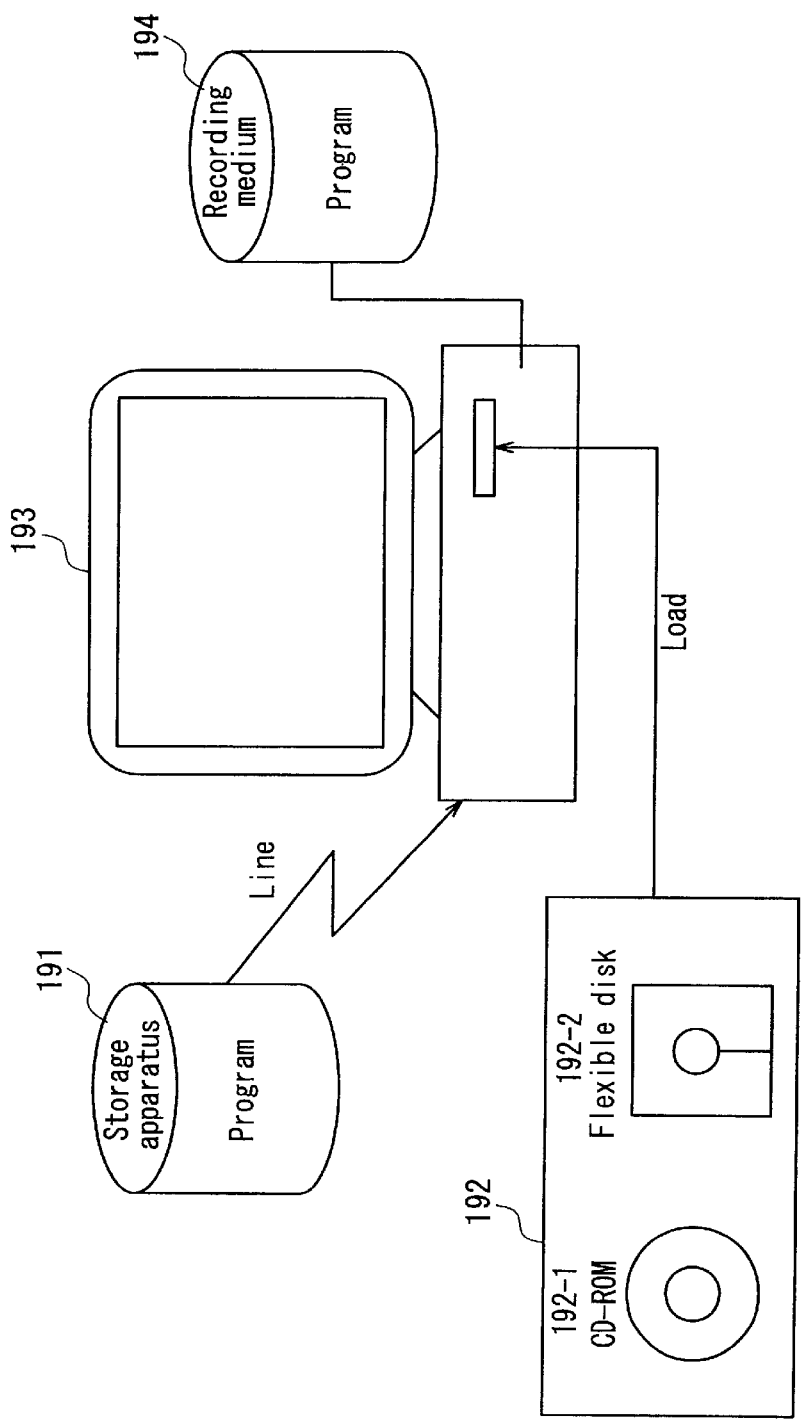
FIG. 19 illustrates a computer execution environment.
Figure 20:
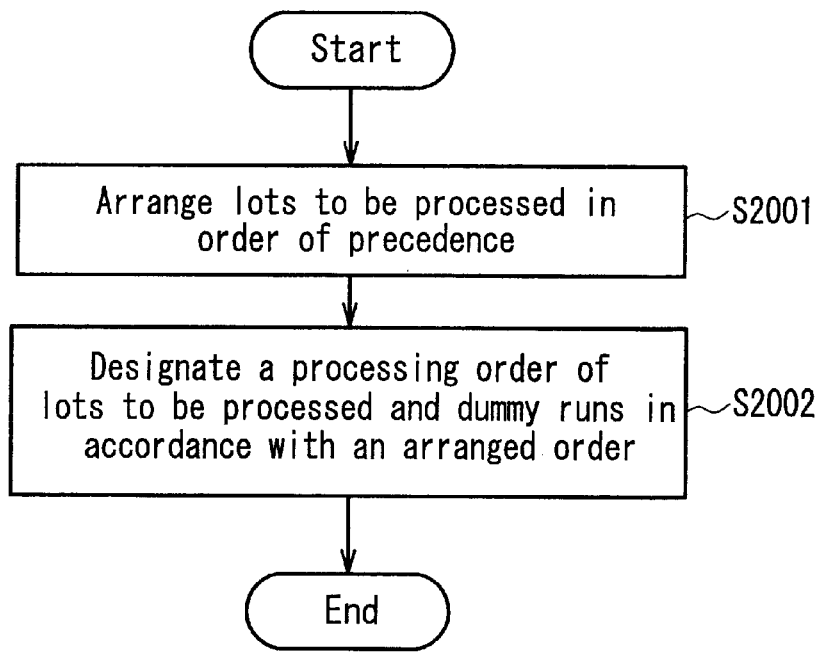
FIG. 20 is a flow chart illustrating processing in a conventional production management method.
Figure 21:
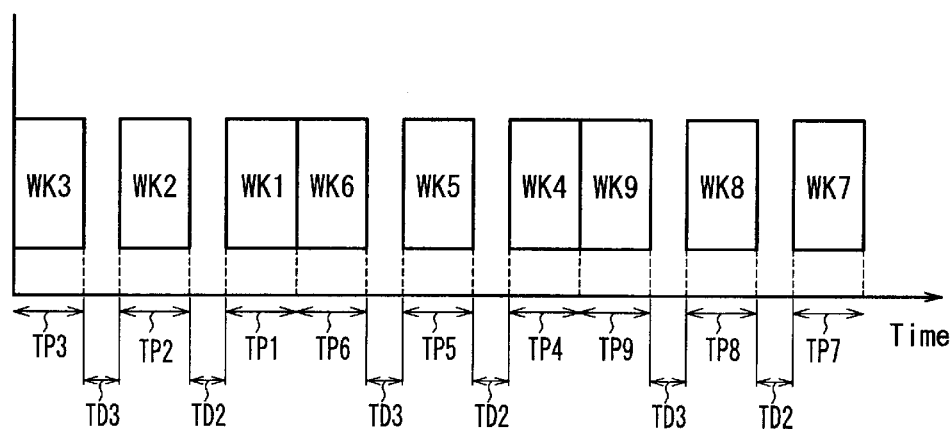
FIG. 21 is a time chart designating a lot processing order in a conventional production management method.

In any of the embodiments, a program for realizing the production management method of the present invention may be stored not only in a portable recording medium 192 such as a CD-ROM 192-1 and a flexible disk 192-2, but also in another storage apparatus 191 provided at the end of a communication line and a recording medium 194 such as a hard disk and a RAM of a computer 193, as shown in FIG. 19. During execution, the program is loaded and executed on a main memory.

Furthermore, the contamination degree definition information, the contamination degree setting information on an operation basis, the contamination change setting information on a dummy run basis, the operation setting information on an equipment basis, the dummy run setting information on an equipment basis, the information on lots to be processed on an equipment basis, and the like used in the production management method of the present invention also may be stored not only in a portable recording medium 192 such as a CD-ROM 192-1 and a flexible disk 192-2, but also in another storage apparatus 191 provided at the end of a communication line and a recording medium 194 such as a hard disk and a RAM of a computer 193, as shown in FIG. 19. For example, such information is read by the computer 193 in executing the production management method of the present invention.

As described above, according to the production management method of the present invention, the processing order of lots is designated considering the contamination degree in each operation for processing the lots, whereby the processing number and the processing time of dummy runs can be reduced, the operating ratio of equipment can be enhanced, and the lead time of a lot can be shortened, and furthermore, production costs can be reduced due to the reduction in the number of dummy wafers to be used for dummy runs.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A production management method, applied to production equipment for performing a plurality of production operations having different processing conditions in the same processing chamber, the method comprising:

previously determining a definition of a contamination degree that is an index representing how a product or the production equipment is contaminated in the production operations;

setting a contamination degree of a product or the production equipment after processing the product in the production operations, with respect to each of the production operations;

recording the contamination degree set for each of the production operations;

recording information for products to be processed, together with information on the corresponding production operations for processing the respective products;

grouping a plurality of the products to be processed in the production operation having the same contamination degree after processing into one contamination group;

recording grouping information for the products with respect to a result of the grouping; and designating execution of processing in the production operations on the basis of the grouping information so that the products of the same contamination group are processed sequentially.

2. The production management method according to claim 1, wherein, in a case where the production equipment executes batch processing, one batch process is executed for each contamination group.

3. A production management method, applied to production equipment for performing a plurality of production operations having different processing conditions in the same processing chamber, the method comprising:

previously determining a definition of a contamination degree that is an index representing how a product or the production equipment is contaminated in the production operations;

setting a contamination degree of a product or the production equipment after processing the product in the production operations, with respect to each of the production operations;

recording the contamination degree set for each of the production operations;

recording information for products to be processed, together with information on the corresponding production operations for processing the respective products;

sorting a plurality of the products in increasing order of the contamination degree after processing of the corresponding production operations;

recording sorting information on an order of the products as a sorting result; and designating execution of processing in the production operations in accordance with the information on the order of the products in the sorting result.

4. The production management method according to claim 3, wherein, in a case where the production equipment adopts a single wafer system, the products are processed successively one by one in accordance with information on the order of the products in the sorting result.

5. A production management method, applied to production equipment for performing a plurality of production operations having different processing conditions in the same processing chamber, the method comprising:

previously determining a definition of a contamination degree that is an index representing how a product or the production equipment is contaminated in the production operations;

setting a contamination degree of a product or the production equipment after processing the product in the production operations, with respect to each of the production operations;

recording the contamination degree set for each of the production operations;

recording information for products to be processed, together with information on the corresponding production operations for processing the respective products;

grouping a plurality of the products to be processed in the production operation having the same contamination degree after processing into one contamination group;

recording grouping information for the products with respect to a result of the grouping on the basis of the contamination group;

sorting a plurality of the products in increasing order of the contamination degree after processing by the corresponding production operations;

recording sorting information on an order of the products as a sorting result; and designating execution of processing in the production operations in accordance with the information on the order of the products as the result of the sorting.

6. The production management method according to claim 5, wherein, in a case where the production equipment performs batch processing, one batch process is executed for each contamination group.

7. The production management method according to claim 5, wherein, in a case where the production equipment adopts a single wafer system, the products are processed successively one by one in accordance with the information on the order of the products in the sorting result.

8. A production management method, applied to production equipment for performing a plurality of production operations having different processing conditions in the same processing chamber, the method comprising:

previously determining a definition of a contamination degree that is an index representing how a product or the production equipment is contaminated in the production operations;

setting a contamination degree of a product or the production equipment after processing the product in the production operations, with respect to each of the production operations;

recording the contamination degree set for each of the production operations;

recording information for products to be processed, together with information on the corresponding production operations for processing the respective products;

grouping a plurality of the products capable of complying with a delivery date even if an order is changed into one delivery date group;

recording delivery date grouping information on the products with respect to a result of the grouping on a basis of the delivery date group;

sorting the delivery date groups in increasing order of remaining number of days to a delivery date from the delivery date group whose delivery date to be met is earliest;

recording delivery date sorting information on an order of the delivery date groups as a sorting result;

grouping a plurality of the products to be processed in the production operation having the same contamination degree after processing into one contamination group on a basis of the delivery date group;

recording contamination grouping information for the products with respect to a result of the grouping on the basis of the contamination group;

sorting a plurality of the products in increasing order of the contamination degree after processing of the corresponding production operations;

recording contamination sorting information on an order of the products as a sorting result; and designating execution of processing in the production operations in accordance with the order of the delivery date sorting result and the order of the products in the contamination sorting result.

9. The production management method according to claim 8, wherein, in a case where the production equipment performs batch processing, one batch process is executed for each contamination group.

10. The production management method according to claim 8, wherein, in a case where the production equipment adopts a single wafer system, the products are processed successively one by one in accordance with the order of the products in the contamination sorting result.

11. The production management method according to claim 8, wherein the recording of the delivery date grouping information products in the second storage apparatus includes:

sorting the delivery date groups in increasing order of remaining number of days to a delivery date from the delivery date group whose delivery date to be met is earliest, and recording information on an order of the delivery date groups as a sorting result;

grouping a plurality of the products, which include the product whose delivery date to be met is earliest and are capable of complying with the earliest delivery date to be met even when being replaced by the product whose delivery date to be met is earliest, into a first delivery date group, and recording information on the products on a basis of the first delivery date group; and repeatedly executing further classified grouping based on a delivery date in the same way as in grouping into the first delivery date group among the remaining products that do not belong to the first delivery date group.

* * * * *